US009550007B2

(12) United States Patent
Tsai et al.

(10) Patent No.: US 9,550,007 B2
(45) Date of Patent: Jan. 24, 2017

(54) METHODS AND SOLUTIONS FOR RAPIDLY KILLING OR DEACTIVATING SPORES (71) Applicant: EP Technologies LLC, Akron, OH (US)

(72) Inventors: Tsung-Chan Tsai, Cuyahoga Falls, OH (US); Sameer Kalghatgi, Fairlawn, OH (US); Daphne Pappas Antonakas, Hudson, OH (US); Robert L. Gray, Hudson, OH (US)

(73) Assignee: EP Technologies LLC, Akron, OH (US)

( * ) Notice: Subject to any disclaimer, the term of this patent is extended or adjusted under 35 U.S.C. 154(b) by 0 days.

(21) Appl. No.: 14/775,942

(22) PCT Filed: Mar. 17, 2014

(86) PCT No.: PCT/US2014/030361
§ 371 (c)(1),
(2) Date: Sep. 14, 2015

(87) PCT Pub. No.: WO2014/145570
PCT Pub. Date: Sep. 18, 2014

(65) Prior Publication Data
US 2016/0022850 A1    Jan. 28, 2016

Related U.S. Application Data (63) Continuation of application No. 13/843,189, filed on Mar. 15, 2013, now Pat. No. 9,339,572.

(51) Int. Cl.
*A61L 9/00* (2006.01)
*A61L 2/00* (2006.01)
(Continued)

(52) U.S. Cl.
CPC .......... *A61L 2/14* (2013.01); *A01N 31/00* (2013.01); *A01N 59/00* (2013.01); *A01N 61/00* (2013.01);
(Continued)

(58) Field of Classification Search
CPC .......... A61L 2/00; A61L 2/22; A61L 9/16
(Continued)

(56) References Cited

U.S. PATENT DOCUMENTS 3,918,987 A   11/1975   Kopfer
4,020,856 A    5/1977   Masterson
(Continued)

FOREIGN PATENT DOCUMENTS

WO       0110215      2/2001
WO      02059046      8/2002
(Continued)

OTHER PUBLICATIONS

Venezia, Richard, et al., "Lethal Activity of Nonthermal Plasma...", Univ. of Chicago Press, Infection Control and Hospital Epidemiology, vol. 29, No. 5, May 2008, http://www.jstor.org/stable/10.1086/588003.
(Continued)

*Primary Examiner* — Monzer R Chorbaji
(74) *Attorney, Agent, or Firm* — Calfee, Halter & Griswold LLP (57) ABSTRACT Exemplary methods and systems for killing or deactivating spores include applying a fluid to a surface containing a spore; and applying direct or indirect plasma to the surface for a period of time. In some embodiments, the fluid includes water. In some embodiments, the spore is *Clostridium difficile* and in some is *Bacillus Anthracis*. In some embodiments, the fluid is in the form of a vapor, a fog, a spray, a mist or an aerosol, which may be activated prior to or after
(Continued)

applying the fluid to a surface. In some embodiments, peroxynitrite is created in the fluid during the method. Another exemplary embodiment of killing or deactivating a spore includes treating spores with direct plasma or indirect plasma for a period of time and applying an antimicrobial to the spores. In some embodiments, the antimicrobial is an alcohol, a bleach or an alcohol-based sanitizer.

18 Claims, 5 Drawing Sheets

(51) Int. Cl.
| | |
|---|---|
| B01J 19/08 | (2006.01) |
| A61L 2/14 | (2006.01) |
| A01N 59/00 | (2006.01) |
| A01N 31/00 | (2006.01) |
| A01N 61/00 | (2006.01) |
| A61L 2/18 | (2006.01) |

(52) U.S. Cl.
CPC ............ *A61L 2/0011* (2013.01); *A61L 2/0088* (2013.01); *A61L 2/18* (2013.01)

(58) Field of Classification Search
USPC ...................... 422/1, 4, 186.04, 305–306, 28
See application file for complete search history.

(56) References Cited

U.S. PATENT DOCUMENTS

| | | | |
|---|---|---|---|
| 5,281,315 | A | 1/1994 | Krapivina et al. |
| 5,876,663 | A | 3/1999 | Laroussi |
| 6,030,506 | A | 2/2000 | Bittenson et al. |
| 6,171,625 | B1 | 1/2001 | Denvir et al. |
| 6,176,941 | B1 | 1/2001 | Jewett et al. |
| 6,387,238 | B1 | 5/2002 | Merk |
| 6,543,460 | B1 | 4/2003 | Denes et al. |
| 6,706,243 | B1 | 3/2004 | Sias et al. |
| 6,723,091 | B2 | 4/2004 | Goble et al. |
| 6,911,225 | B2 | 6/2005 | Ruan et al. |
| 7,004,356 | B1 | 2/2006 | Sayers |
| 7,008,592 | B2 | 3/2006 | Sias et al. |
| 7,163,664 | B2 | 1/2007 | Paskalov et al. |
| 7,291,314 | B2 | 11/2007 | Paskalov et al. |
| 7,326,383 | B2 | 2/2008 | Gunter et al. |
| 7,569,203 | B2 | 8/2009 | Fridman et al. |
| 7,608,839 | B2 | 10/2009 | Coulombe et al. |
| 7,829,051 | B2 | 11/2010 | Fridman et al. |
| 7,989,673 | B2 | 8/2011 | Paskalov et al. |
| 8,048,930 | B2 | 11/2011 | Bobbert |
| 8,354,057 | B2 | 1/2013 | Heselton et al. |
| 8,383,036 | B2 | 2/2013 | Sloan et al. |
| 8,388,618 | B2 | 3/2013 | Fridman et al. |
| 2004/0120844 | A1 | 6/2004 | Tribelsky et al. |
| 2004/0216845 | A1 | 11/2004 | Golkowski et al. |
| 2006/0189976 | A1 | 8/2006 | Karni et al. |
| 2006/0223729 | A1 | 10/2006 | Hamblin et al. |
| 2006/0229225 | A1 | 10/2006 | Martin |
| 2007/0251953 | A1 | 11/2007 | Criswell et al. |
| 2009/0041617 | A1 | 2/2009 | Lee |
| 2009/0054896 | A1 | 2/2009 | Fridman et al. |
| 2009/0175956 | A1 | 7/2009 | Buschmann et al. |
| 2010/0145253 | A1 | 6/2010 | Gutsol et al. |
| 2010/0168499 | A1 | 7/2010 | Gutsol et al. |
| 2010/0196505 | A1 | 8/2010 | Kaiser et al. |
| 2010/0209293 | A1 | 8/2010 | Ikawa et al. |
| 2010/0280513 | A1 | 11/2010 | Juergen et al. |
| 2010/0296977 | A1 | 11/2010 | Hancock |
| 2011/0112528 | A1 | 5/2011 | Stieber et al. |
| 2011/0171188 | A1 | 7/2011 | Morfill et al. |
| 2011/0251604 | A1 | 10/2011 | Staack et al. |
| 2012/0039747 | A1 | 2/2012 | Morfill et al. |
| 2012/0042419 | A1 | 2/2012 | Wilson et al. |
| 2012/0100037 | A1 | 4/2012 | Shannon et al. |
| 2012/0305787 | A1 | 12/2012 | Henson |
| 2012/0315684 | A1 | 12/2012 | Hayashi et al. |

FOREIGN PATENT DOCUMENTS

| | | | |
|---|---|---|---|
| WO | 2006076334 | 7/2006 | |
| WO | 2006116252 | 11/2006 | |
| WO | 2007048806 | 5/2007 | |
| WO | 2007063987 | 6/2007 | |
| WO | 2010009103 | 1/2010 | |
| WO | 2010022160 | 2/2010 | |
| WO | WO2010085513 | 7/2010 | |
| WO | 2010107722 | 9/2010 | |
| WO | 2010107741 | 9/2010 | |
| WO | 2010107744 | 9/2010 | |
| WO | 2010107745 | 9/2010 | |
| WO | 2010107746 | 9/2010 | |
| WO | 2012018891 | 2/2012 | |
| WO | 2012112042 | 8/2012 | |
| WO | WO 2012/018891 A2 * | 9/2012 | ............ A01N 37/44 |

OTHER PUBLICATIONS

Lawley, Trevor, D., et al., "Proteomic and Genomic Characterization of Highly Infectious . . .", J. Bacteriol. 2009, vol. 191, No. 17, pp. 5377-5386, Jun. 2009, http://jb.asm.org/content/191/17/5377.

Oehmigen, K., et al., "The Role of Acidification for Antimicrobial . . .", Wiley InterScience, Plasma Process. and Polym. 2010, 7, pp. 250-257, 2010.

Lawley, Trevor, D., et al., "Use of Purified Clostridium difficile Spores . . . ", Appl. Environ. Microbiol., pp. 6895-6900, Aug. 2010.

Ermolaeva, Svetlana, A., et al., "Bactericidal effects of non-thermal argon plasma . . . ", J. Med. Microbiol., Sep. 2010, http://jmm.sgmjournals.org/content/60/1/75.full.

Traylor, Matthew, J., et al., "Long-term antibacterial efficacy of air plasma-activated water", J. Phys. D: Appl. Phys., Nov. 2011, http://www.stacks.iop.org/JPhysD/44/472001.

Huang, Yaohua, "Non-thermal Plasma Inactivation of Bacillus Amyloliquefaciens Spores", Master's Thesis, Univ. of Tennessee, 2011, http://www.trace.tennessee.edu/utk_gradthes/980.

Tolls, Elisabeth, H., et al., Surface Layers of Clostridium difficile Endospores, J. Bacteriol. 2011, vol. 193, No. 23, pp. 6461-6470, 2011.

Paredes-Sabja, D., et al., "Adherence of Clostridium difficile spores to Caco-2 cells in culture", J. Med. Microbiol., pp. 1208-1218, 2012.

Pei., X., et al., "Inactivation of a 25.5 . . . Enterococcus faecalis biofilm . . . ", J. Phys. D: Appl. Phys., http://www.stacks.iop.org/JPhysD/45/165205, Apr. 2012.

Escobar-Cortes, K., et al., "Proteases and sonication specifically remove the exosporium layer . . . ", J. Microbiol. Methods, Jan. 2013.

International Search Report and Written Opinion from International Application No. PCT/US2013/063360, date of mailing Dec. 11, 2013.

Burlica et al. "Formation of H2 and H202 in a Water-Spray Gliding Arc Nonthermal Plasma Reactor", Industrial & Engineering Chemistry Research, vol. 49, No. 14, Jun. 24, 2010.

Klimpel, Kurt, M.D. "Clostridium difficile Test Exposure to BIT Plasma"; Plasma Clostridium difficile Killing Trials; 2009; 5 pages.

Alekseev, Oleg et al., "Nonthermal Dielectric Barrier Discharge (DBD) Plasma Suppresses Herpes Simplex Virus Type 1 (HSV-1) Replication in Corneal Epithelium", TVST, 2014, vol. 3, No. 2, Article 2, pp. 1-14.

Alhabshan, Rashed et al., "Effects of In-vivo Application of Cold Atmospheric Plasma on Corneal Wound Healing in New Zealand White Rabbits", International Journal of Ophthalmic Pathology, 2013, 2:3, pp. 1-5.

Brun, Paolo et al., "Disinfection of Ocular Cells and Tissues by Atmospheric-Pressure Cold Plasma", PLoS ONE, Mar. 2012, vol. 7, Issue 3, e33245, pp. 1-13.

(56) References Cited

OTHER PUBLICATIONS

Critzer, Faith J. et al., "Atmospheric Plasma Inactivation of Foodborne Pathogens on Fresh Produce Surfaces", Journal of Food Protection, vol. 70, No. 10, 2007, pp. 2290-2296.
Delaquis, Pascal J. et al., "Disinfection of Mung Bean Seed with Gaseous Acetic Acid", Journal of Food Protection, vol. 62, No. 8, 1999, pp. 953-957.
Park, Dayonna P. et al., "Reactive nitrogen species produced in water by non-equilibrium plasma increase plant growth rate and nutritional yield", Current Applied Physics 13 (2013), pp. 519-529.
Sera, Bozena et al., "Germination of Chenopodium Album in Response to Microwave Plasma Treatment", Plasma Science and Technology, vol. 10, No. 4, Aug. 2008, pp. 506-511.EA.
Niemira, Brendan A., Cold Plasma Inactivates Salmonella Stanley and *Escherichia coli* O157:h7 Inoculated on Golden Delicious Apples, Journal of Food Protection, vol. 71, No. 7, 2008, pp. 1357-1365.
International Search Report and Written Opinion from International Application No. PCT/US2014/030361, date of mailing Jul. 16, 2014.

\* cited by examiner

METHODS AND SOLUTIONS FOR RAPIDLY KILLING OR DEACTIVATING SPORES

RELATED APPLICATIONS

This application claims the benefits of and priority to U.S. patent application Ser. No. 13/843,189, entitled Methods and Solutions for Killing or Deactivating Spores, filed on Mar. 15, 2013, which is incorporated herein in its entirety by reference.

TECHNICAL FIELD

The present invention relates generally to methods and solutions for rapid killing or deactivating spores.

BACKGROUND OF THE INVENTION

Spore formation is a sophisticated mechanism by which some Gram positive bacteria survive conditions of external stress and nutrient deprivation by producing a multi-layered protective capsule enclosing their dehydrated and condensed genomic DNA. When such bacterial spores encounter a favorable environment, germination can take place enabling the bacteria to reproduce, and, in the case of pathogenic species, cause disease. Bacterial spores possess a coat and membrane structure that is highly impermeable to most molecules that could be toxic to the dormant bacteria. Therefore, spores are highly resistant to damage by heat, radiation, and many of the commonly employed anti-bacterial agents, and generally can only be destroyed by some severe chemical procedures including oxidizing vapors such as hydrogen peroxide, chlorine dioxide and ozone.

People receiving medical care can acquire serious infections called healthcare-associated infections (HAIs). While most types of HAIs are declining, one—caused by the germ *Clostridium difficile*, "*C. difficile*"—remains at historically high levels. *C. difficile* is linked to 14,000 American deaths each year. Those most at risk are people, especially older adults, who take antibiotics and also receive long term medical care.

*C. difficile* is an anaerobic, Gram positive bacterium. Normally fastidious in its vegetative state, it is capable of sporulating when environmental conditions no longer support its continued growth. The capacity to form spores enables the organism to persist in the environment (e.g., in soil and on dry surfaces) for extended periods of time.

Current methods of killing or deactivating *C. difficile* include applying bleach, liquid solutions containing hydrogen peroxide, and other biocidal compounds, and/or ultraviolet radiation (UV) to *C. difficile* for a period of time longer than 3 minutes.

Anthrax spores, *Bacillus anthracis* ("*B. anthracis*") is the pathogenic organism that causes anthrax. Anthrax is a disease that is frequently fatal due to the ability of this bacterium to produce deadly toxins. *B. anthracis* also forms spores. Inhalation of anthrax spores is frequently fatal, particularly if treatment is not started prior to the development of symptoms.

Anthrax spores are also among the most difficult spores to kill or deactivate. Present methods of killing or deactivating anthrax spores use of pressurized steam at elevated temperatures, topical treatment with highly caustic concentrated sodium hypochlorite solutions or with certain disinfecting foam products.

One of the reasons it is very difficult to kill or deactivate dry spores is due to their tendency to aggregate and form multilayered structures. In addition, the dry spores adhere to surfaces and skin very strongly, making it very difficult to physically remove them.

SUMMARY

Exemplary methods and systems for killing or deactivating spores include applying a fluid to a surface containing a spore; and applying direct plasma to the surface for a period of time.

Additional exemplary methods and systems for killing or deactivating spores include applying a fluid to a surface containing a spore; and applying indirect plasma to the surface for a period of time.

In some embodiments, the fluid includes water. In some embodiments, the spore is *Clostridium difficile* and in some it is *Bacillus anthracis*. In some embodiments, the fluid is in the form of droplets, such as, for example, aerosol, fog, mist, or spray and in some it is in the form of a vapor. In some embodiments, peroxynitrite is created in the fluid during the method. In some embodiments, peroxynitrite and several other oxygen and nitrogen derivatives are created in the fluid during the method.

Another exemplary embodiment of killing or deactivating a spore includes treating spores with direct plasma or indirect plasma for a period of time and applying an antimicrobial to the spores. In some embodiments, the antimicrobial is an alcohol, a bleach or alcohol based sanitizer.

Another exemplary embodiment of killing or deactivating a spore includes passing a mixture of one or more gases and droplets of a liquid through non-thermal plasma to activate the gas/droplet mixture and applying the activated gas/droplet mixture onto a surface containing a spore for a period of time.

Another exemplary embodiment of killing or deactivating a spore includes passing a mixture of one or more gases and droplets of a liquid through non-thermal plasma to activate the gas/droplet mixture, condensing the activated droplets in container to create the activated liquid, and applying the activated liquid onto a surface containing a spore for a period of time.

Another exemplary method of killing or deactivating spores includes passing a mixture of one or more gases and droplets of a liquid through a non-thermal plasma and applying the activated gas/droplet mixture onto a surface containing one or more spores for a period of time. In addition, the distance between the non-thermal plasma and the surface is such that the gas/droplet mixture passing through the non-thermal plasma reaches the surface in less than about 3 times the half-life of short lived reactive species generated as the gas/droplet mixture passes through the plasma.

Another exemplary method of killing or deactivating spores includes passing a mixture of one or more gases and droplets of a fluid through a non-thermal plasma to activate the gas/droplet mixture and applying the activated gas/droplet mixture onto a surface containing one or more spores for a period of time that is less than about 1 minute.

BRIEF DESCRIPTION OF THE DRAWINGS

These and other features and advantages of the present invention will become better understood with regard to the following description and accompanying drawings in which.

DETAILED DESCRIPTION

Plasmas, or ionized gases, have one or more free electrons that are not bound to an atom or molecule. Plasmas may be generated using a variety of gases including, air, nitrogen, noble gases (He, Ar, Xe, Kr, etc), oxygen, carbon dioxide and mixtures thereof under an applied electric field. In addition, non-thermal plasmas provide high concentrations of energetic and chemically active species. They can operate far from thermodynamic equilibrium where the temperature of free electrons in the plasma is significantly higher than neutral atoms, ions and molecules. Such plasmas have high concentrations of active species and yet remain at a temperature that is substantially the same as room temperature. The energy from the free electrons may be transferred to additional plasma components initiating additional ionization, excitation and/or dissociation processes. Fluid that is contacted with plasma becomes "activated" and is referred to herein as plasma activated fluid, and in some embodiments, the plasma activated fluid is plasma activated water.

In some embodiments, plasmas may contain superoxide anions [$O2^-$], which react with $H^+$ in acidic media to form hydroperoxy radicals, $HOO^-$ [$O_2^-$]+[$H^+$]→[$HOO^-$]. Other radical species may include $OH^-$ and $NO^-$ in aqueous phase or the presence of air or gas. Treating water with plasma results in plasma activated water that may contain concentrations of one or more of ozone, $H_2O_2$, nitrates, nitrites, radicals and other active species.

Activating water with plasma to obtain plasma activated water is shown and described in co-pending U.S. Non-Provisional application Ser. No. 13/829,877 titled Sanitization Station Using Plasma Activated Fluid, filed on Mar. 14, 2013, which claims priority to U.S. Provisional Application Ser. No. 61/621,078 also titled Sanitization Station Using Plasma Activated Fluid, filed on Apr. 6, 2012 and co-pending U.S. Non-Provisional application Ser. No. 13/842,574 titled Methods of Making Solutions to Kill or Deactivate Spores Microorganisms, Bacteria and Fungus, filed on Mar. 15, 2013 and U.S. Provisional Application Ser. No. 61/710,263 also titled Solutions and Methods of Making Solutions to Kill or Deactivate Spores Microorganisms, Bacteria and Fungus, filed on Oct. 5, 2012. All of which are incorporated by reference herein in their entirety. Several other patents and applications such as: PCT Application Nos. WO 02/059046, titled Method of Activation of Chemically Pure and Potable Water and filed on Jan. 25, 2002; WO 2007/048806, titled Method for the Preparation of Biocidal Activated Water Solutions and filed Oct. 25, 2006; WO 2012/018891, which is titled Materials for Disinfection Produced by Non-Thermal Plasma and was filed on Aug. 3, 2011; and U.S. Pat. No. 7,291,314, titled Activated Water Apparatus and Methods and filed Dec. 20, 2001, are incorporated herein by reference in their entirety for their disclosure on activating fluid.

Figure 1:
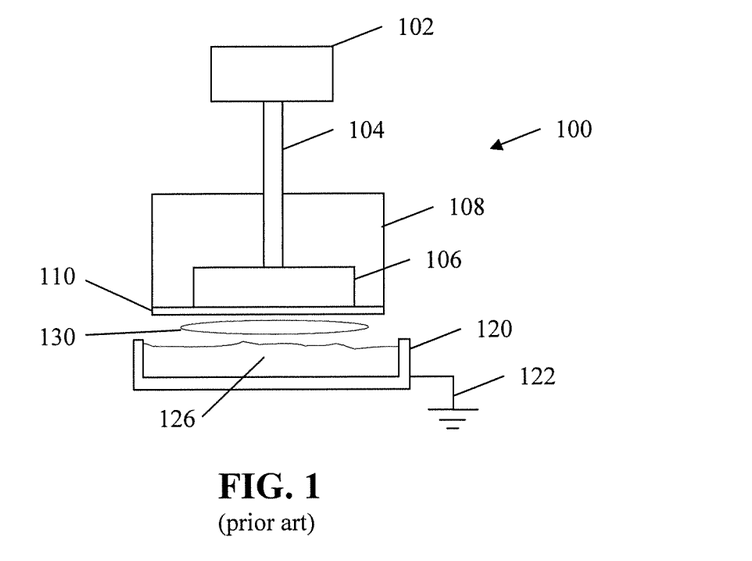
FIG. 1 illustrates a prior art embodiment for creating activated water using direct plasma.

It is known to treat water and other fluids with plasma to "activate" them. One method of activating water and other liquids is illustrated in FIG. 1, which is a prior art dielectric barrier discharge ("DBD") plasma generating system 100. The prior art plasma generating system 100 includes a high voltage source 102, a conductor 104, a housing 108, a high voltage electrode 106 and a dielectric barrier 110. It should be noted that the discharge can be generated with and without the presence of dielectric barrier 110. The plasma generating system 100 also includes a container 120, which is grounded with grounding conductor 122. During operation, the high voltage source 102 is turned on and plasma 130 forms below the dielectric barrier 110. High voltage power source 102 may be a DC power source, a high frequency AC power source, an RF power source, a pulsed DC power source, a pulsed AC power source, a microwave power source or the like. The power supply can be pulsed with a duty cycle of 0-100% and in some embodiments, a pulse duration of 1 nanosecond up to 10 microseconds.

The plasma contacts the water or fluid 126 and activates the water or fluid 126. Fluid 126 activated by direct contact with plasma is referred to herein as "direct plasma activated fluid."

Figure 2:
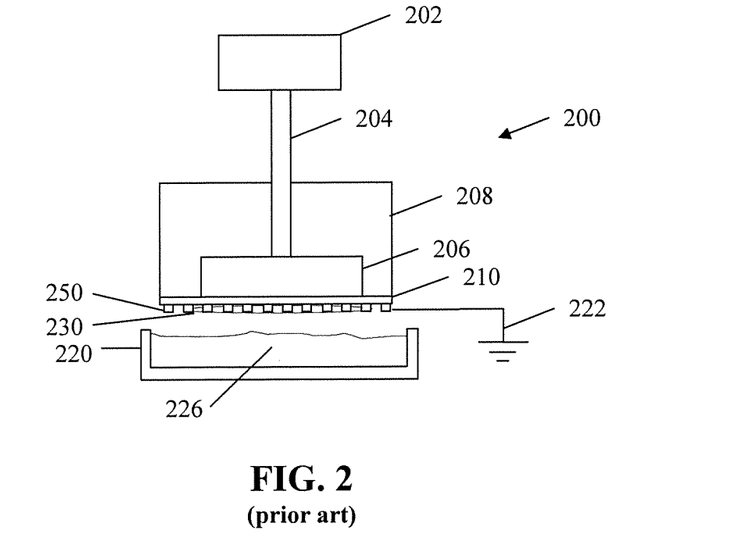
FIG. 2 illustrates a prior art embodiment for creating activated water using indirect plasma.

FIG. 2 illustrates an exemplary prior art system 200 for activating a fluid using indirect plasma. System 200 includes a high voltage power source 202. High voltage power source 202 may be a DC power source, a high frequency AC power source, an RF power source, a microwave power source, a pulsed DC power source, a pulsed AC power source or the like. The power supply can be pulsed with a duty cycle of 0-100% and in some embodiments, a pulse duration of 1 nanosecond up to 10 microseconds.

The exemplary system 200 includes a DBD plasma generator 208 connected to high voltage power source 202 by cable 204. DBD plasma generator 208 includes a high voltage electrode 206 and a dielectric barrier 210 located between high voltage electrode 206 and the fluid 226 that is to be activated. A filter 250 is also included. Filter 250 is a conductive mesh that is grounded by grounding conductor 222.

During operation of system 200, when high voltage electrode 206 is energized, plasma 230 forms below the dielectric barrier 210, and the filter 250 (if the filter 250 is made of a conductive material and grounded) prevents charged ions and electrons from passing through and contacting the fluid 226 to be activated. Thus, only neutral species pass through and activate the fluid 226. This is typically referred to as "afterglow" or "indirect" plasma. In some embodiments, the fluid is water. Fluid 226 activated by afterglow that passes through, or is created through filter 250, is referred to "indirect plasma activated fluid."

Figure 3:
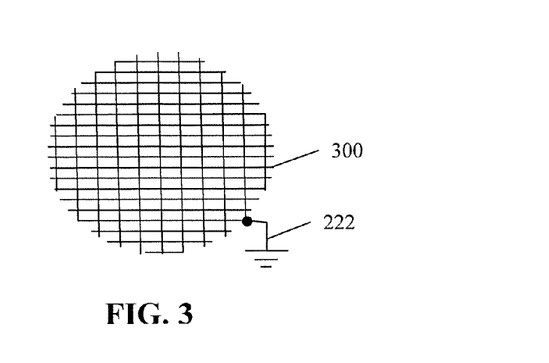
FIG. 3 illustrates an exemplary mesh filter for use in the exemplary embodiment of FIG. 2.

The experimental data provided below generated by indirect plasma, utilized a copper mesh as a filter. FIG. 3 illustrates the exemplary copper mesh 300 that was utilized as filter 250. The copper mesh was a copper woven wire having a 16×16 mesh with a 0.011" wire diameter and a 0.052" opening size (67% opening area). A mesh with different conducting materials, wire diameters and opening sizes may be used.

In the exemplary embodiments disclosed herein the fluid may be water. In some embodiments, the properties of the fluid may be altered prior to activation by plasma or indirect plasma to increase or decrease concentration of species, radicals and the like. For example, the pH of water may be adjusted to be acidic or basic. The pH may be adjusted by, for example, adding acid to the water prior to activation. The pH level may be lowered through the activation process. In one embodiment, the pH level of the activated water is about 2.0, in another the pH is between about 2.0 and 3.5, and in yet another is about 2.7. Still, in another the pH is less than about 3.0 and in another embodiment is less than about 2.0. In one embodiment, the pH is about 2.0.

In addition, the properties of the activated fluid may be adjusted during the activation process itself by altering the gas that is ionized at the electrode. For example, the gas that is ionized may be normal air, $N_2$, $O_2$, He, Ar, Xe, Kr, vaporized liquids (water, ethanol and others), combinations thereof at various ratios, or the like. In some embodiments, one or more inert gases are used in the plasma generating process. In some embodiments, one or more noble gases are used in the plasma generating process, and in some embodiments, combinations of noble gases and vaporized liquids are used in the plasma generating process.

Further, additives may be added before or after the fluid is activated to increase efficacy or stabilization of the resulting solution. Other additives that may be used depending on the desired results include, for example, alcohol, silver salts, e.g., silver nitrate or silver chloride, or colloidal silver; zinc salts, e.g. zinc chloride, zinc lactate, or zinc oxide; suspensions containing metal nanoparticles; chlorhexidine; anionic, cationic, non-ionic and/or amphoteric surfactants; emulsifiers; hydrotropes; glycerol; chelating agents; alcohols; quaternary ammonium compounds, acids (organic or inorganic); bases; or surface tension decreasing agents. In some embodiments, ethanol, acidified ethanol, n-propanol or isopropanol may be used as an additive to increase efficacy. In addition, it is believed that the addition of these ethanol additives may increase the half-life of radical species that aid in the killing and deactivation of spores.

In some embodiments, the additive comprises, such as, for example, a volatile additive, like alcohol, which will not leave a residue on the surface after the surface has been treated.

Fluid 226 may be a source of water, or of water with additional additives. In one embodiment, the fluid is tap water, however, the water may be distilled water, deionized water, tap water, filtered water, saline, water with acidic properties, water with basic properties or water mixed with additives such as, for example, alcohol. In addition, other additives may be used to optimize reactive species generation or increase performance and/or increase stability. These additives may include, for example chelators to reduce metal degradation; surfactants to improve penetration of the solution, to reduce the impact of organic load and/or buffers used to adjust the pH. In addition, in some embodiments corrosion inhibitors may be added, such as, for example, inorganic sulfates, inorganic phosphates. In some embodiments, a zeolite buffering system may be used. In some embodiments, one or more of these additives are added prior to activation of the water.

Figure 4:
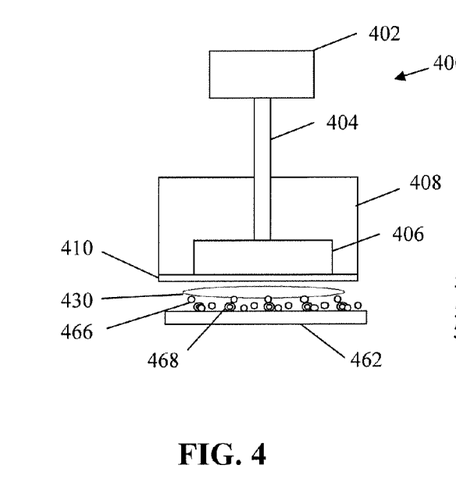
FIGS. 4 and 4A illustrate an exemplary system and method for killing or deactivating spores.

FIG. 4 illustrates an exemplary embodiment of a system 400 for killing or deactivating spores 468 on a surface 462. The spore may be, for example, *Clostridium difficile* "C. diff," *Bacillus anthracia* "Anthrax" or other spores. The spores are dry spores, and in some cases, layers of dried spores. The surface may be any surface, including for example, surfaces in a hospital or nursing home like stainless steel, glass, ceramic, linens, curtains, rubber, fabric, plastics, or the like. In some embodiments, the surface may be skin or tissue.

The system 400 includes a high voltage source 402 connected to an electrode 406 by cable 404, a dielectric barrier 410 and a housing 408. System 400 is used to kill or deactivate spores 468 that have been wetted by droplets or vapor 466. The operating methodology is described with respect to FIG. 4A below.

Figure 4A:
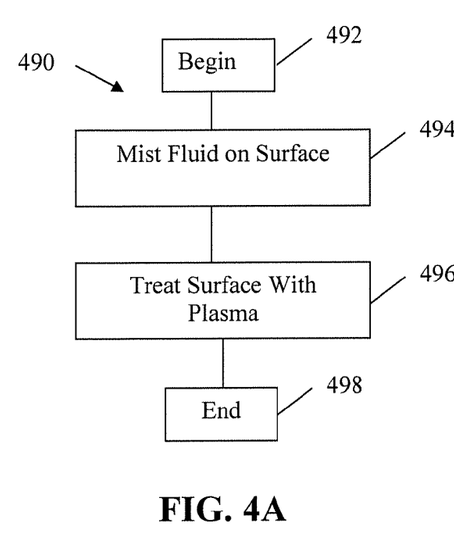
Figure 5:
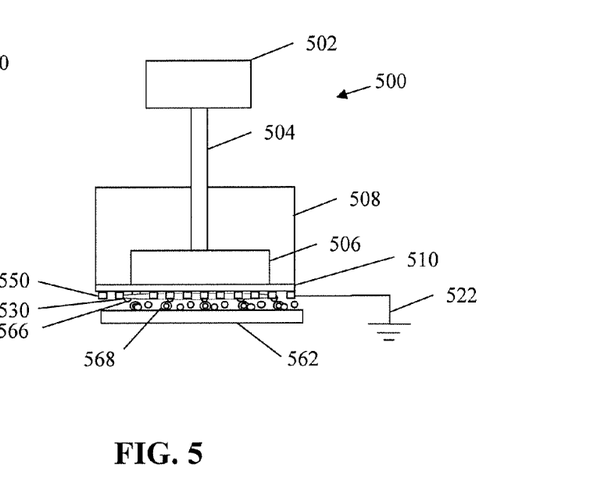
FIGS. 5 and 5A illustrate an exemplary system and method for killing or deactivating spores.
Figure 5A:
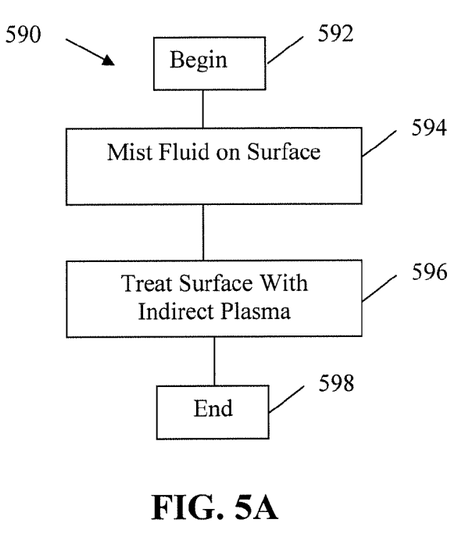
Figure 6:
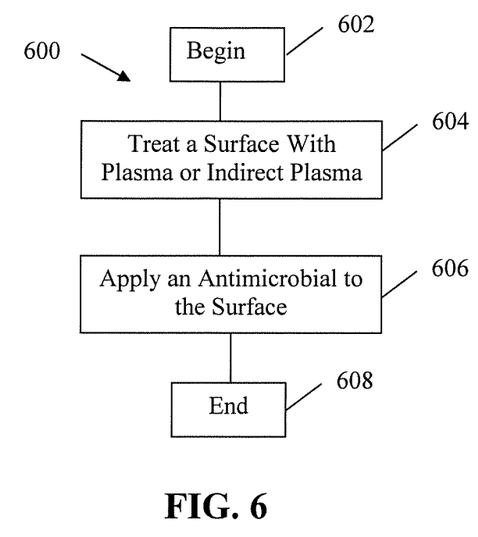
FIG. 6 illustrates another exemplary methodology for killing or deactivating spores.

FIG. 4A illustrates an exemplary methodology 490 for killing a spore using direct plasma. The methodology begins at block 492. At block 494 fluid is placed on a dry surface containing spores to be treated. In some embodiments, the fluid is in a fog, mist or sprayed droplet form. The droplet size can vary and in some embodiments is between about 1 nanometers and 1 micrometer in diameter (fog). In some embodiments the diameter size is between about 1 micrometer and 100 micrometers (mist), and in some embodiments is between about 100 micrometer and 1 millimeter (spray). In some embodiments, the fluid is a vapor. Although the droplet size for fog, mist and spray are identified for exemplary embodiments, the terms should not be construed to be limited to the identified droplet sizes. In addition, as used herein, the fog, mist or spray may be in the form of an aerosol. In some embodiments, the fluid is water. In some embodiments, the fog, mist, or spray of fluid covers the top layer of spores and forms a thin liquid film over the spores. In some embodiment, the fog, mist, or spray of fluid forms individual small droplets over the spores. In some embodiments, the fog, mist, or spray of fluid covers only a portion of the spores. In some embodiments, the fluid is water with one or more of the additives identified above. In some embodiments, the pH of the fluid is adjusted prior to applying the fluid on the spores. In some embodiments, the droplets in the fluid are electrostatically charged. Applying an electrostatic charge to the fluid causes the droplets to repel one another. The result is that the fluid is evenly distributed on the surface.

The surface may be any surface, such as, for example, table, a bed, etc. made of polymer, metal, rubber, glass, silicone, fabric material or the like. The surface may be a hard surface or a soft surface, such as, for example, linens, curtains and the like. In addition, the surface may be tissue or skin. After a fluid is applied to the surface in the form of a fog, mist, spray or vapor, the surface is treated with direct plasma at block 496. The direct plasma may be generated from air, nitrogen, an inert gas, a noble gas or any combinations thereof as described above.

Treatment time may vary depending on the surface. In some embodiments, the surface is treated for about 5 minutes. In some embodiments, the surface is treated for less than about 5 minutes. In some embodiments, the surface is treated for less than about 3 minutes. In some embodiments, the surface is treated for less than about 1 minute. In some embodiments, the surface is treated for about 30 seconds or less. In some embodiments, the surface is treated for more than about 5 minutes. After the surface has been treated, the methodology ends at block 498.

Treating the surface activates the fluid (e.g., water) and elements, such as nitrogen and oxygen in the air creating highly reactive radical and non-radical, charged and neutral species (e.g., reactive nitrogen and reactive oxygen species), which penetrate the shell of the spore and kill or deactivate the spores. In some embodiments, the plasma contacts the spores directly between droplets or vapor and creates an opening for the activated fluid to penetrate the shell of the spore to kill or deactivate the spore.

In some embodiments, the methodology 490 generates peroxynitrite, which has a half-life of around 1 second. The fluid surface coverage depends on the surface tension of the applied liquid and the surface energy of the material that is exposed to it. It can range from partial surface wetting, due to the formation of spherical drops spaced apart from each other, to complete wetting through the formation of a thin water film that can result from coalescence of droplets. Liquid droplets possess a relatively large surface area compared with bulk fluid in container, and the large surface to volume ratio allows the plasma to activate the fluid droplets quickly and more effectively, as higher concentrations of reactive oxygen and nitrogen species such as ozone, hydrogen peroxide, nitrites and nitrates are generated. It also allows the generation of peroxynitrite, which almost immediately contacts the spore surface, as opposed to having to migrate through a larger volume of water to make contact with the spores. Thus, the peroxynitrite may contact the spore prior to its degeneration.

Figure 7:
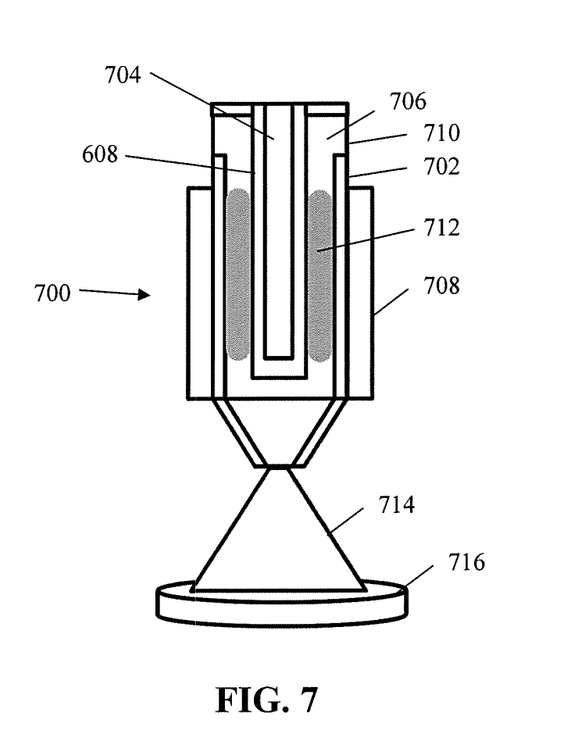
FIG. 7 illustrates an exemplary embodiment of an apparatus for generating activated gas/droplet mixture for killing or deactivating spores.

FIG. 5 illustrates an exemplary embodiment of a system 500 for killing or deactivating spores 568 on a surface 562. The spores are dry spores, and in some cases are layers of dry spores. The spore may be, for example, *C. difficile*, anthrax or other spores. The system 500 includes a high voltage source 502 connected to an electrode 506 by cable 504, a dielectric barrier 510, a housing 508 and a filter 550. System 500 is used to kill or deactivate spores 568 that have been wetted by droplets or vapor 566. The operating methodology is described with respect to FIG. 5A below.

FIG. 5A illustrates an exemplary methodology 590 for killing a spore using indirect plasma. The methodology begins at block 592. At block 594 fluid is placed on a dry surface containing spores to be treated. In some embodiments, the fluid is in a fog, mist or spray form. The droplet size can vary and in some embodiments is between about 1 nanometers and 1 micrometer in diameter (fog). In some embodiments the diameter size is between about 1 micrometer and 100 micrometers (mist), and in some embodiments is between about 100 micrometer and 1 millimeter (spray). In some embodiments, the fluid is a vapor. Although the droplet size for fog, mist and spray are identified for exemplary embodiments, the terms should not be construed to be limited to the identified droplet sizes. In addition, as used herein, the fog, mist or spray may be in the form of an aerosol. In some embodiments, the fluid is water. In some embodiments, the fog, mist, or spray of fluid covers the top layer of spores and forms a thin liquid film over the spores. In some embodiment, the fog, mist, or spray of fluid forms individual small droplets over the spores. In some embodiment, the fog, mist, or spray of fluid covers only a portion of the spores. In some embodiments, the fluid is water with one or more of the additives identified above. In some embodiments, the pH of the fluid is adjusted prior to applying the fluid on the spores. In some embodiments, the droplets in the fluid are electrostatically charged. Applying an electrostatic charge to the fluid causes the droplets to repel one another. The result is that the fluid is evenly distributed on the surface.

The surface may be any surface as described above with respect to FIGS. 4 and 4A. After the surface has been wetted with a fluid, the surface is treated with indirect plasma at block 596. The indirect plasma may be generated from air, nitrogen, a reactive gas, a noble gas or any combinations thereof as described above.

Treatment time may vary depending on the surface. In some embodiments, the surface is treated for about 5 minutes. In some embodiments, the surface is treated for less than about 5 minutes. In some embodiments, the surface is treated for less than about 3 minutes. In some embodiments, the surface is treated for less than about 1 minute, and in some embodiments less than about 30 seconds. In some embodiments, the surface is treated for more than about 5 minutes. After the surface has been treated, the methodology ends at block 598.

Treating the surface activates the fluid, which penetrates the shell of the spore and kills or deactivates the spores. In some embodiments, the indirect plasma or afterglow contacts the spores directly between fluid droplets or fluid vapor and creates an opening for the activated fluid to penetrate the shell of the spore to kill or deactivate the spore.

In some embodiments, the methodology 590 generates peroxynitrite, which has a half-life of around 1 second. The fluid droplets has a relatively large surface area compared with bulk fluid in container, and the large surface area allows the indirect plasma or afterglow to activate the fluid droplets quickly and more effectively, as higher concentrations of reactive oxygen and nitrogen species such as ozone, hydrogen peroxide, nitrites and nitrates are generated. It also allows the peroxynitrite to almost immediately contact the spore surface, as opposed to having to migrate through a larger volume of water to make contact with the spores. Thus, the peroxynitrite may contact the spores before it degenerates.

FIG. 6 illustrates another exemplary methodology for killing or deactivating spores. The methodology begins at block 602. At block 604 a surface is exposed to plasma. The surface may be treated with indirect plasma or direct plasma. The treatment time may be for about 1 minute. In some embodiments, the treatment time may be less than about 1 minute, and in some embodiments less than about 30 seconds. The treatment time may be between about 1 minute and 3 minutes. In some embodiments, the treatment time is about 5 minutes. Still in some embodiments, the treatment time is between about 3 and 5 minutes, and in some embodiments, the treatment time is more than about 5 minutes.

After the treatment has ended, an antimicrobial is applied to the surface. The antimicrobial may be for example, alcohol based sanitizer; alcohol; bleach; silver salts, e.g., silver nitrate or silver chloride, or colloidal silver; zinc salts, e.g. zinc chloride, zinc lactate, or zinc oxide; suspensions containing metal nanoparticles; chlorhexidine; anionic, cationic, non-ionic and/or amphoteric surfactants; emulsifiers; hydrotopes; glycerol; chelating agents; quatenary ammonium compounds, acids (organic or inorganic); bases; or surface tension decreasing agents; or the like. In some embodiments, the antimicrobial may be applied to the surface prior to treating the surface with direct or indirect plasma. The methodology ends at block 608.

In some embodiments, a filter having a carulite catalyst to filter out ozone may replace the prior art filter 250. Other materials and/or coatings may be used to block certain species in the plasma from passing through to the fluid. In some embodiments, multiple filters are utilized, thus a copper filter could be used to filter out charged particles and a second carulite coated mesh could be used to filter out ozone. In addition, a wire mesh may be used for electromagnetic shielding. In some embodiments, the filter is conductive and is used to tune the electric field between the plasma generator and conductive filter to control the density and/or concentrations of reactive species that pass through the filter.

FIG. 7 illustrates an exemplary embodiment of an apparatus 700 for generating activated gas/droplet mixture for rapidly killing or deactivating spores. The droplets may be a mist, spray, fog, aerosol, or the like. Apparatus 700 includes a housing 702. Located within housing 702 is a high voltage electrode 704. High voltage electrode 704 is connected to a power supply (not shown). An exemplary power supply is a high voltage AC sinusoidal power supply. In some embodiments, the power source may be a high frequency AC power source, an RF power source, a pulsed DC power source, a pulsed AC power source or the like. A dielectric barrier 705 surrounds high voltage electrode 704. Apparatus 700 includes a grounded electrode 708, a fluid inlet 710 to allow a mixture of gas and liquid droplets to flow in, a passage 706 that extends from the fluid inlet 710 past electrode 704 and to outlet 703. When the high voltage electrode 704 is energized, plasma 712 is generated in passage 706. The mixture of gas and liquid droplets passing through the plasma 712 is activated and the activated gas/droplet mixture 714 flows out of outlet 703 onto surface 716.

The surface 716 may be any surfaces containing bacterial spores, including for example, surfaces in a hospital or nursing home like stainless steel, glass, ceramic, linens, curtains, rubber, fabric, plastics, or the like. In some embodiments, the surface may be skin or tissue. The spore may be, for example, *Clostridium difficile* "*C. diff.*," *Bacillus anthracis* "Anthrax" or other spores. The spores are dry spores, and in some cases, layers of dried spores.

The surface 716 is exposed to the activated gas/droplet mixture 714. The exposure time may be for about 1 minute. In some embodiments, the exposure time may be less than about 1 minute, and in some embodiments less than about 30 seconds. The exposure time may be between about 5 seconds and 30 seconds. In some embodiments, the exposure time is 5 seconds. Still in some embodiments, the exposure time is less than about 2 seconds, and in some embodiments, the exposure time is between about 1 and 2 seconds.

In some embodiments, the gas/droplet mixture flowing into inlet 710 is water droplets and air containing nitrogen and oxygen. In some embodiments, the gas/droplet flowing into inlet 710 is water and an additive, such as, for example ethanol and air containing nitrogen and oxygen.

It is believed that the activated gas/droplet mixture 714 contains a significant amount of reactive species with short half-lives, such as for example, nitrogen species, such as nitrites and peroxynitrite. The half-life of peroxynitrite is short at about 1 second. It is believed that in some embodiments, the short-lived active species provide for rapid killing or deactivating spores.

In some embodiments, the outlet 703 of apparatus 700 is located at a distance from the surface containing spores so that the gas/droplet mixture contacts the surface within about 3 times the half life of the short lived reactive species. In the case of peroxynitrite, for example the time of the gas/droplet mixture to travel the distance from the outlet 703 to the surface would be less than about 3 seconds. In some embodiments, the distance is a distance that allows the activated gas/droplet mixture to reach the surface within about one half-life of the active species. In some embodiments, the distance is less than about 15 centimeters.

In these embodiments, the activated gas/droplet mixture 714 contains small amounts of $H_2O_2$. In some embodiments, the amount of $H_2O_2$ is between about 3 and about 10 ppm. In some embodiments, the $H_2O_2$ is less than about 50 ppm.

In some embodiments, the air may be replaced with, or mixed with, a gas, such as, for example a noble gas or a vaporized liquid.

In some embodiments, the liquid droplets in the activated gas/droplet mixture 714 are electrostatically charged. Applying an electrostatic charge to the fluid causes the particles to repel one another. The result is the droplets are evenly distributed on the surface. In addition, the electrostatically charged particles have the tendency to wrap around the edges of the surface, and in some cases around the bottom of the surface of three-dimensional objects. Such applications may be desirable, in for example, hospitals, so the activated gas/droplet mixture 714 treats all around a bed rail or an arm-rest.

In some embodiments, the activated droplets in the mixture 714 form individual droplets over the surfaces. In some embodiments, the activated droplets form a thin film over the surface. In some embodiments, the thickness of the film is less than about 500 microns.

Figure 8:
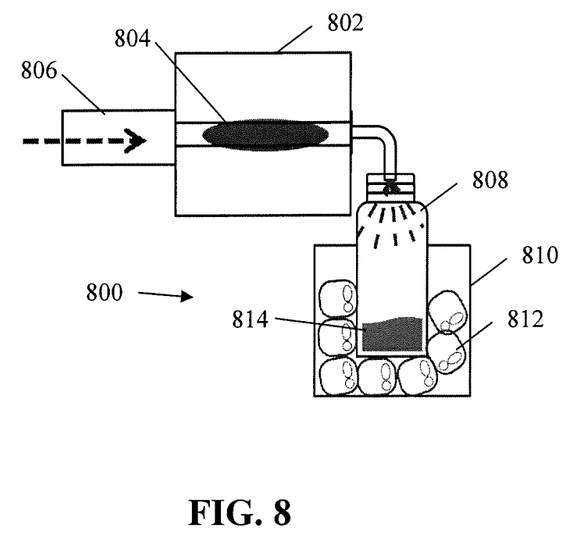
FIG. 8 illustrates an exemplary embodiment of an apparatus for generating activated liquid for killing or deactivating spores.

FIG. 8 illustrates an exemplary apparatus 800 for generating activated fluid for killing or deactivating spores. Apparatus 800 includes a plasma generator 802 that generates plasma 804. Apparatus 800 also includes a fluid inlet 806. As described above, the fluid, e.g. gas/droplet mixture, flowing through plasma 804 becomes an activated gas/droplet mixture 805. Activated gas/droplet mixture 805 flows into container 808, which is resting in an ice bath 812 in container 810. The activated droplets in the gas/droplet mixture 805 condense in container and become activated liquid 814.

Experimental Results

An alternating polarity pulsed power supply was used in the experiment to generate plasma. The pulse frequency was 3.5 kHz and the pulse duration was 10 µs. The amplitude of the voltage pulse was 20 kV peak to peak with a 5 V/ns rise time. The gap distance between the plasma generating system and the treated surface was about 1 to 2 mm. The experiments used air as the plasma working gas under the pressure of 1 atmosphere, which is the ambient pressure.

Experimental results demonstrated the ability to kill or deactivate *C. diff.* with the exemplary systems and methodologies described herein. In one case, deactivation was observed after only 30 seconds of exposure to plasma.

*C. diff* spores were applied on stainless steel coupons and microscope slide surfaces. A volume of 10 µl of *C. diff* spores (~$10^8$ CFU/ml) in sterile water was added onto the sterile surfaces and left to dry for 30 min. The dry spores formed a visible spore area with about 3.5 mm in diameter and about 10 mm in diameter on the stainless steel coupons and the microscope slide surfaces, respectively. The dry spores have different diameters on the stainless steel coupon and the microscope slide due to their different hydrophobicity. Then the contaminated surfaces were exposed to plasma as described below. After treatment, the coupons and slides were placed in test tubes filled with neutralizer (9.9 ml). The test tubes were sonicated for 1 minute and vortexed for 15 seconds to fully remove the spores from the surfaces. The neutralizer solution containing spores was diluted and plated on Brain Heart Infusion Agar supplemented with 0.1% Sodium Taurocholate (BHIT). Anaerobic incubation for 36-48 hr was then performed at 37° C., followed by the estimation of surviving colony forming units (CFU).

In one experiment, *C. difficile* was placed on stainless steel coupons and allowed to dry for about 30 minutes. As illustrated in the chart below, a first stainless steel coupon with the *C. difficile* was treated with indirect plasma for a 1 minute period of time resulting in a log reduction of 0.43 colony forming units per milliliter (CFU/ml). A second stainless steel coupon with *C. difficile* was treated with indirect plasma for 5 minutes resulting in a log reduction of 0.63 CFU/ml. Next, another stainless steel coupon with *C. difficile* was treated with direct plasma for a 1 minute period of time resulting in a log reduction of 0.45 CFU/ml. In addition, a fourth stainless steel coupon with *C. difficile* was treated with direct plasma for 5 minutes resulting in a log reduction of 1.11 CFU/ml. These test results, demonstrate that while plasma and indirect plasma alone will kill or deactivate some spores, plasma and indirect plasma alone do not provide the best results.

| Plasma Type | Treatment Time | Apply fluid on spores? | Log Reduction (CFU/ml) | Surface |
|---|---|---|---|---|
| Indirect | 1 min | No | 0.43 | Stainless Steel |
| Indirect | 5 min | No | 0.63 | Stainless Steel |
| Direct | 1 min | No | 0.45 | Stainless Steel |
| Direct | 5 min | No | 1.11 | Stainless Steel |

Next, as illustrated in the chart below, a stainless steel coupon with dry *C. difficile* spores was wetted with water spray and treated with direct plasma for a 30 second, 1 minute or 3 minute period of time, each of which resulted in a log reduction of 3.43, 4.48 and 4.48 CFU/ml respectively. The amount of water covering the spores was less than 5 μl. Each of these values represents the upper limit of the test used. Similarly, an additional stainless steel coupon with *C. difficile* was wetted with water spray and treated with indirect plasma for 3 minutes, which resulted in a log reduction of 4.18 CFU/ml, for 1 minute which resulted in a 3.33 log reduction and for 3 minutes resulting in a 2.48 log reduction. Thus, wetting the spores with fluid and then treating with plasma or indirect plasma resulted in significant killing or deactivating of the *C. difficile* spores.

In another experiment, a microscope glass slide with dry *C. difficile* spores was wetted with water spray and treated with direct plasma for 3 minutes, which resulted in a log reduction of 4.00 CFU/ml. Thus, wetting the spores on glass with fluid and then treating with plasma or indirect plasma resulted in a significant killing or deactivating of the *C. difficile* spores.

| Plasma Type | Treatment Time | Apply fluid on spores? | Log Reduction (CFU/ml) | Surface |
|---|---|---|---|---|
| Direct | 30 sec | Yes | 3.43** | Stainless Steel |
| Direct | 1 min | Yes | 4.48** | Stainless Steel |
| Direct | 3 min | Yes | 4.48** | Stainless Steel |
| Indirect | 3 min | Yes | 4.18** | Stainless Steel |
| Indirect | 1 min | Yes | 3.33 | Stainless Steel |
| Indirect | 3 min | Yes | 2.48 | Stainless Steel |
| Direct | 1 min | Yes | 3.06 | Glass |
| Direct | 3 min | Yes | 4.00** | Glass |

**Denotes Upper limit of the measurement scale for the test results.

In another experiment as indicated in the chart below, a stainless steel coupon with dry *C. difficile* spores was treated for 1 minute with direct plasma and then treated for 4 minutes with an alcohol based sanitizer (which alone did not show any killing efficacy in *C. difficile*) and the result was a 2.71 CFU/ml log reduction in *C. difficile* spores. Thus, pre-treating spores with plasma and then with applying an antimicrobial to the spores results in a significant kill or deactivation of the spores.

| Plasma Type | Treatment Time | Alcohol applied to Spores | Log Reduction (CFU/ml) | Surface |
|---|---|---|---|---|
| Direct | 1 min | Yes | 2.71 | Stainless Steel |

Additional experiments were conducted to determine efficacy of killing or deactivating different types of spores. These experiments involved applying about 3 μl de-ionized ("DI") water on several different types of spores, which were inoculated on stainless steel coupons, and applying direct plasma to the film of water to achieve a greater than 6 log reduction, which is a complete destruction of the spores on the stainless steel coupons. The power supply settings were 3.5 kHz, 10 μs pulsed duration with 100% duty cycle. The fluid was activated in the presence of air and accordingly the air surrounding the fluid was also activated. The results are shown in the table below.

| Spore Type | Treatment Time | Log Reduction (CFU/ml) | Surface |
|---|---|---|---|
| *C. difficile* | 30 seconds | >6.32 | Stainless Steel coupon |
| *Bacillus subtilis* ("*B. subtilis*") | 60 seconds | >6.43 | Stainless Steel coupon |
| *Bacillus cereus* ("*B. cereus*") | 90 seconds | >6.28 | Stainless Steel coupon |

The results demonstrate that complete kill of spores may be achieved rapidly in an efficient manner by applying water to a surface and activating the fluid.

In addition, experiments were also conducted using additives to determine efficacy of certain additives on different surfaces. Excised porcine skin was tested as a surrogate to human skin to target applications that involve hand sanitization. In each of these experiments, fluid was applied to a dry surface containing dry *C. difficile* spores and direct plasma was applied to the fluid in the presence of air, which contains nitrogen and oxygen. The power supply used in the experiments was an AC sinusoidal power supply. The power supply has a number of settings ranging from a scale 1 to a scale 60 that correspond to a voltage of 1 kV to 30 kV. Additional settings include the driving frequency (f) and the duty cycle. The experiments were conducted by placing the water, or water with the additive on the spores and applying plasma to the water or water and additive for 30 seconds.

| | | Without Additive | | With Additive | |
|---|---|---|---|---|---|
| Power Supply Setting | Surface | Method | Log Reduction (CFU/ml) | Method | Log Reduction (CFU/ml) |
| Scale 15, f = 20.5 kHz, 100% duty cycle | *C. difficile* spores on soiled* stainless steel coupons | 3 μl water + 30 second exposure to plasma | 0.20 | 3 μl with 70% ethanol + 30 second exposure to plasma | 2.85 |
| Scale 30, f = 20.5 kHz, | *C. difficile* on pigskin | 10 μl water + 30 second | 0.70 | 30 μl with 70% ethanol in $H_2O$ | 1.29 |

-continued

| Power Supply Setting | Surface | Without Additive | | With Additive | |
|---|---|---|---|---|---|
| | | Method | Log Reduction (CFU/ml) | Method | Log Reduction (CFU/ml) |
| 50% duty cycle | | exposure to plasma | | (v/v)% + 30 second exposure to plasma | |
| Scale 30, f = 20.5 kHz, 50% duty cycle | C. difficile on pigskin | 10 μl water + 30 second exposure to plasma | 0.70 | 30 μl with 70% acidified (pH 1.5) ethanol in $H_2O$ (w/w)% + 30 second exposure to plasma | 3.90 |
| Scale 30, f = 20.5 kHz, 50% duty cycle | C. difficile on pigskin | 10 μl water + 30 second exposure to plasma | 0.70 | 30 μl with 70% isopropanol in $H_2O$ (v/v)% + 30 second exposure to plasma | 1.26 |
| Scale 30, f = 20.5 kHz, 50% duty cycle | C. difficile on pigskin | 10 μl water + 30 second exposure to plasma | 0.70 | 30 μl with 70% n-propanol in $H_2O$ (v/v)% + 30 second exposure to plasma | 1.85 |

*ASTM soil method: the soil contains 5 μl bovine serum albumin, 20 μl bovine mucin, and 7 μl Tryptone.

As can be seen from the results, ethanol, acidified ethanol, n-propanol and isopropanol additives all increased the efficacy of spore kill.

In addition to pigskin, other surfaces including leather, vinyl, nylon, polyester, and microfiber were tested utilizing the present method, all resulted in a >4 log kill when a film of water was applied to the dry spores and then treated with plasma for 30 seconds.

Several additional experiments were conducted with organic soil loads. In all of the experiments, a thin film of water was placed on the dry surface (stainless steel coupon) that contained dry C. difficile spores mixed with an organic soil load (fetal bovine serum) and then plasma was applied to the surface for 30 seconds. With a 1% organic load mixed with the spores, the average log reduction (CFU/ml) was a 4.53 log reduction. With a 5% organic load, the average log reduction was greater than a 4.63. With a 10% organic load, the average log reduction was 2.14.

In yet additional experiments by passing a mixture of gas and liquid droplets through plasma applicants were able to achieve a kill or deactivation of a greater than 5 log reduction (test detection limit) of the C. difficile spores on dry stainless steel coupons, representing a complete kill or deactivation of spores on the coupons in as little as 2 seconds.

In these experiments, the power supply used in the experiments was an AC sinusoidal power supply. The power supply has a number of settings ranging from a scale 1 to a scale 60 that correspond to a voltage of 1 kV to 30 kV. Additional settings include the driving frequency (f) and the duty cycle. The fluid was activated by passing a mixture of air and liquid droplets through plasma as described with respect to FIG. 7 above. In this case, the liquids are in the form of a mist since the liquid droplets are generated by an ultrasonic humidifier, having a size of between about 1 micrometer and about 100 micrometers. The chart below provides the experimental results. The first column identifies the power supply settings. The second column identifies the type and the form of the liquid that was activated in the presence of air and the third column indicates the amount of time the activated air/droplet mixture was applied to the dry spores. The fourth column identifies the "hold time" that the activated droplets was allowed to remain on the spores after the fluid was turned off. The fifth column indicates the log reduction in spores that was observed. As can be seen, water with the proper power supply settings is capable of obtaining a complete kill or deactivation of the C. difficile spores on the stainless steel coupons. In addition, a water ethanol mixture demonstrated increased efficacy with a wider range of power supply settings.

| Power Supply Setting | Fluid | Treatment Time | Hold Time | Log Reduction (CFU/ml) |
|---|---|---|---|---|
| Scale 12, f = 22 kHz, 50% duty cycle | Water Mist | 2 seconds | 0 seconds | 2.37 |
| Scale 9, f = 22 kHz, 100% duty cycle | Water Mist | 2 seconds | 0 seconds | <2.00 |
| Scale 12, f = 22 kHz, 50% duty cycle | Water Mist | 2 seconds | 30 seconds | >5.18 |
| Scale 9, f = 22 kHz, 100% duty cycle | Water Mist | 2 seconds | 30 seconds | <2.00 |
| Scale 9, f = 22 kHz, 100% duty cycle | 35% Ethanol Mist | 1 second | 0 seconds | 3.00 |
| Scale 9, f = 22 kHz, 100% duty cycle | 35% Ethanol Mist | 1 second | 30 seconds | 3.39 |
| Scale 12, f = 22 kHz, 50% duty cycle | 35% Ethanol Mist | 2 seconds | 0 seconds | >5.18 |
| Scale 9, f = 22 kHz, 100% duty cycle | 35% Ethanol Mist | 2 seconds | 30 seconds | >5.18 |
| Scale 12, f = 22 kHz, 50% duty cycle | 35% Ethanol Mist | 2 seconds | 0 seconds | >5.18 |
| Scale 9, f = 22 kHz, 100% duty cycle | 35% Ethanol Mist | 2 seconds | 30 seconds | >5.18 |

The results demonstrate a very rapid complete kill of spores by embodiments of the present invention. Note that in these studies a volume of 10 μl of C. diff spores (7.18 $\log_{10}$ CFU/ml) was placed onto the stainless steel coupon. Thus, 5.18 log reduction represented the kill or deactivation of all the spores on the coupon.

In addition, experiments were conducted to demonstrate that in some embodiments, the gap between the plasma generating electrode and the surface might be about 15 mm. In some embodiments, the gap may be about 10 mm. In some embodiments the gap may be about 5 mm. Larger gap distances may be utilized in some embodiments.

In yet another experiment, the activated mist was collected in a container in an ice bath as described with respect to FIG. 8. The activated water was applied to a surface with dry *C. difficile* spores for 1 minute, which resulted in a 3.27 log reduction. It is believed that the activated water collected by condensing the activated mist is not as effective as the mist at killing and deactivating the spores because the short half-lives of some of the reactive species caused those species to degenerate during the time it took to condense and be applied to the dry spores.

While the present invention has been illustrated by the description of embodiments thereof and while the embodiments have been described in considerable detail, it is not the intention of the applicants to restrict or in any way limit the scope of the appended claims to such detail. Additional advantages and modifications will readily appear to those skilled in the art. Moreover, elements described with one embodiment may be readily adapted for use with other embodiments. Therefore, the invention, in its broader aspects, is not limited to the specific details, the representative apparatus and/or illustrative examples shown and described. Accordingly, departures may be made from such details without departing from the spirit or scope of the applicants' general inventive concept.

We claim:

1. A method of killing or deactivating spores comprising:
    passing a mixture of one or more gases and droplets of a liquid through a non-thermal plasma to activate the gas/droplet mixture;
    applying the activated gas/droplet mixture onto a surface containing one or more spores for a period of time;
    wherein the distance between the non-thermal plasma and the surface is such that the gas/droplet mixture passing through the non-thermal plasma reaches the surface in less than about 3 times the half-life of short lived reactive species generated as the gas/droplet mixture passes through the plasma wherein at least some of the short lived reactive species is peroxynitrite.

2. The method of claim 1 wherein the period of time is a function of the time required to kill or deactivate a desired spore.

3. The method of claim 1 wherein the period of time is less than about 1 minute.

4. The method of claim 1 wherein the period of time is less than about 30 seconds.

5. The method of claim 1 wherein the period of time is less than about 10 seconds.

6. The method of claim 1 wherein the distance is such that droplets passing through the non-thermal plasma reach the surface in less than about the half-life of the short lived reactive species.

7. The method of claim 1 wherein the one or more gases comprises air.

8. The method of claim 1 wherein the one or more gases comprises at least one noble gas.

9. The method of claim 1 wherein the liquid comprises water.

10. The method of claim 1 wherein the liquid comprises an additive.

11. The method of claim 1 wherein the additive comprises one of ethanol, acidified ethanol, n-propanol and isopropanol.

12. A method of killing or deactivating spores comprising:
    passing a mixture of one or more gases and droplets of a fluid through a non-thermal plasma to activate the gas/droplet mixture and
    applying the activated gas/droplet mixture onto a surface containing one or more spores for a period of time that is less than about 1 minute wherein the distance between the non-thermal plasma and the surface is such that the gas/droplet mixture passing through the non-thermal plasma reaches the surface in less than about 3 times the half-life of short lived reactive species generated as the gas/droplet mixture passes through the plasma; wherein at least some of the short lived reactive species is peroxynitrite; wherein the gas/droplet mixture comprises one or more electrostatically charged droplets that cause the droplets to tend to form uniform droplet distribution on the surface to be disinfected.

13. The method of claim 12 wherein the period of time is less than about 30 seconds.

14. The method of claim 12 wherein the period of time is less than about 10 seconds.

15. The method of claim 12 wherein the period of time is less than about 5 seconds.

16. The method of claim 12 wherein after the gas/droplet mixture passes through the non-thermal plasma, the gas/droplet mixture contacts the surface within about 3 seconds.

17. The method of claim 12 wherein after the gas/droplet mixture passes through the non-thermal plasma gas, the gas/droplet mixture contacts the surface within about 2 seconds.

18. The method of claim 12 wherein after the gas/droplet mixture passes through the non-thermal plasma gas, the gas/droplet mixture contacts the surface within about 1 second.

* * * * *